United States Patent
Colin et al.

(10) Patent No.: US 6,589,790 B1
(45) Date of Patent: Jul. 8, 2003

(54) METHOD AND DEVICE FOR FILLING AN ANALYSIS CARD WITH A LIQUID MEDIUM

(75) Inventors: Bruno Colin, Marcy l'Etoile (FR); Cécile Jaravel, Lyons (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/194,726

(22) PCT Filed: Apr. 14, 1998

(86) PCT No.: PCT/FR98/00747
§ 371 (c)(1),
(2), (4) Date: Dec. 2, 1998

(87) PCT Pub. No.: WO98/46977
PCT Pub. Date: Oct. 22, 1998

(30) Foreign Application Priority Data

Apr. 15, 1997 (FR) .............................. 97 04851

(51) Int. Cl.$^7$ ........................... C12M 1/16; C12M 1/18
(52) U.S. Cl. ............................. 436/54; 45/174; 45/180; 422/61; 422/100; 422/102; 141/130; 435/288.4; 435/288.5
(58) Field of Search ............................ 436/54, 45, 180, 436/174; 422/58, 61, 68.1, 81, 99, 100, 102, 103; 435/288.4–288.5; 141/130

(56) References Cited

U.S. PATENT DOCUMENTS

| | | |
|---|---|---|
| 3,860,488 A | 1/1975 | Cooper, III |
| 3,870,602 A | 3/1975 | Froman et al. |
| 3,880,978 A | 4/1975 | Apostoleris et al. |
| 3,942,526 A * | 3/1976 | Wilder et al. ............... 116/110 |
| 3,957,583 A * | 5/1976 | Gibson et al. ......... 195/103.5 R |
| 3,963,355 A | 6/1976 | Aldridge, Jr. et al. |
| D243,542 S | 3/1977 | Fadler et al. |
| D243,543 S | 3/1977 | Fadler et al. |
| 4,018,652 A | 4/1977 | Lanham et al. |
| 4,038,151 A * | 7/1977 | Fadler et al. ............... 195/127 |
| 4,074,940 A | 2/1978 | Tarbet |
| 4,077,845 A | 3/1978 | Johnson |
| 4,090,920 A | 5/1978 | Studer, Jr. |
| 4,116,775 A * | 9/1978 | Charles et al. ....... 195/103.5 M |

(List continued on next page.)

FOREIGN PATENT DOCUMENTS

| | | |
|---|---|---|
| DE | 29 41 177 A1 | 4/1981 |
| DE | 44 29 739 C1 | 3/1996 |
| EP | 0 107 631 A2 | 5/1984 |
| EP | 0 282 840 A2 | 9/1988 |
| EP | 0 445 053 A1 | 9/1991 |
| EP | 0 526 222 A2 | 2/1993 |
| EP | 0 703 052 A1 | 3/1996 |
| EP | 0 745 856 A2 | 12/1996 |
| FR | 2 350 593 | 12/1977 |
| FR | 2 368 774 | 5/1978 |
| GB | 2 025 611 A | 1/1980 |
| WO | WO 83/03677 | 10/1983 |
| WO | WO 88/07351 | 10/1988 |
| WO | WO 90/08308 | 7/1990 |
| WO | WO 94/11489 | 5/1994 |
| WO | WO 94/18369 | 8/1994 |

Primary Examiner—Jill Warden
Assistant Examiner—Kathryn Bex
(74) Attorney, Agent, or Firm—Oliff & Berridge, PLC

(57) ABSTRACT

Device for filling, with a liquid medium (1), an analysis card (2) comprising a body (3) in which at least one reading cavity (3a) is formed, and an orifice (4) communicating with the cavity via at least one internal channel (7), with an external conduit (9) communicating with the orifice, this device comprising an evacuation device (50). It comprises: a connecting device (11) including on one side a joining piece (12) for leaktight and removable coupling to the free end (9a) of the open external conduit, and communicating directly on the other side with the evacuation device (50); a device (34) for closing and re-opening the external conduit.

10 Claims, 3 Drawing Sheets

U.S. PATENT DOCUMENTS

| | | |
|---|---|---|
| 4,118,280 A | 10/1978 | Charles et al. |
| 4,159,875 A | 7/1979 | Hauser |
| D254,687 S | 4/1980 | Fadler et al. |
| 4,207,394 A | 6/1980 | Aldridge, Jr. et al. |
| 4,260,687 A | 4/1981 | Jacobson et al. |
| 4,318,884 A | 3/1982 | Suzuki |
| 4,318,994 A * | 3/1982 | Meyer et al. ............ 435/288.5 |
| 4,327,042 A | 4/1982 | Hagino et al. |
| 4,395,125 A | 7/1983 | Kaneko et al. |
| 4,661,458 A | 4/1987 | Berry et al. |
| 4,693,983 A | 9/1987 | Davies et al. |
| 4,713,974 A | 12/1987 | Stone |
| 4,806,316 A | 2/1989 | Johnson et al. |
| 4,818,493 A | 4/1989 | Coville et al. |
| 4,839,292 A | 6/1989 | Cremonese |
| 4,848,493 A | 7/1989 | Hitchcock |
| 4,912,057 A | 3/1990 | Guirguis et al. |
| 4,912,744 A | 3/1990 | Hurst |
| 4,937,196 A | 6/1990 | Wrasidlo et al. |
| 5,010,014 A | 4/1991 | Gebhardt |
| 5,047,215 A | 9/1991 | Manns |
| 5,079,168 A | 1/1992 | Amiot |
| 5,084,246 A | 1/1992 | Lyman et al. |
| 5,089,413 A | 2/1992 | Nelson et al. |
| 5,110,556 A | 5/1992 | Lyman et al. |
| 5,110,727 A | 5/1992 | Oberhardt |
| 5,120,662 A | 6/1992 | Chan et al. |
| 5,139,951 A | 8/1992 | Butz et al. |
| 5,141,718 A | 8/1992 | Clark |
| 5,168,766 A | 12/1992 | Stoffel |
| 5,180,555 A | 1/1993 | Monget |
| 5,210,021 A | 5/1993 | Goodwin, Jr. |
| 5,219,528 A | 6/1993 | Clark |
| 5,227,137 A | 7/1993 | Monti et al. |
| 5,230,866 A | 7/1993 | Shartle et al. |
| 5,284,753 A | 2/1994 | Goodwin, Jr. |
| 5,290,700 A | 3/1994 | Binot et al. |
| 5,307,144 A | 4/1994 | Hiroshi et al. |
| 5,326,533 A | 7/1994 | Lee et al. |
| 5,330,908 A | 7/1994 | Spaulding |
| 5,336,893 A | 8/1994 | Smith et al. |
| 5,338,666 A | 8/1994 | Monthony et al. |
| 5,340,141 A | 8/1994 | Thorndyke |
| 5,340,747 A | 8/1994 | Eden |
| 5,342,581 A | 8/1994 | Sanadi |
| 5,346,000 A | 9/1994 | Schlitt |
| 5,358,871 A | 10/1994 | Stevens et al. |
| 5,366,893 A | 11/1994 | Stevens et al. |
| 5,374,395 A | 12/1994 | Robinson et al. |
| 5,453,246 A * | 9/1995 | Nakayama et al. ............ 422/63 |
| 5,589,350 A | 12/1996 | Bochner |
| 5,594,183 A * | 1/1997 | Colin ...................... 73/864.52 |
| 5,609,828 A * | 3/1997 | O'Bear et al. .............. 422/102 |
| 5,669,528 A * | 9/1997 | Romero et al. ............. 222/129 |
| 5,746,980 A | 5/1998 | O'Bear et al. |
| 5,804,437 A * | 9/1998 | Tegeler et al. ........... 435/287.1 |
| 5,932,177 A | 8/1999 | O'Bear et al. |
| 5,965,090 A * | 10/1999 | Fanning et al. ................ 422/65 |
| 6,015,531 A * | 1/2000 | Colin et al. ................... 422/58 |
| 6,045,758 A | 4/2000 | Staples et al. |
| 6,124,138 A * | 9/2000 | Woudenberg et al. ... 435/287.2 |
| 6,272,939 B1 * | 8/2001 | Frye et al. ............... 73/864.81 |

* cited by examiner

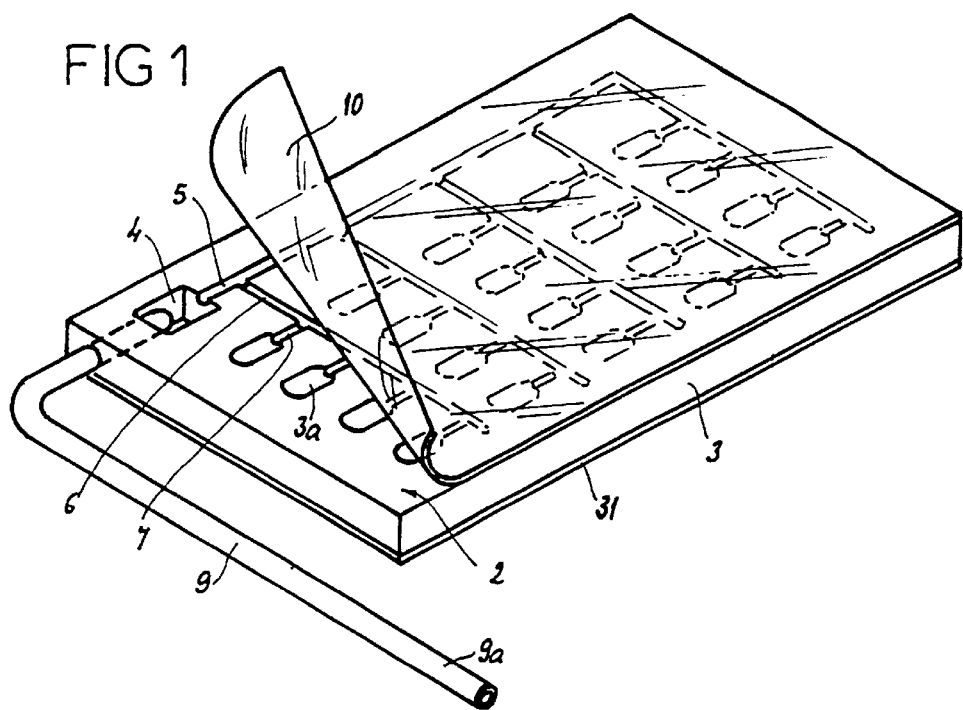
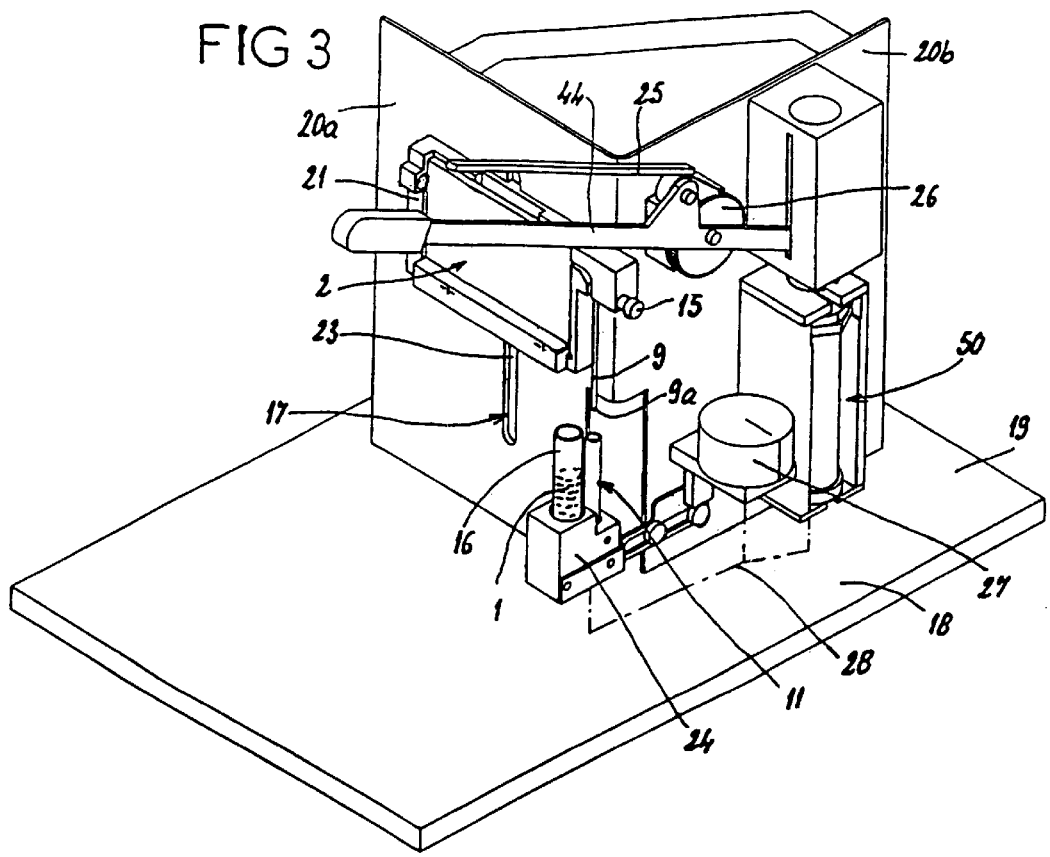

METHOD AND DEVICE FOR FILLING AN ANALYSIS CARD WITH A LIQUID MEDIUM

BACKGROUND OF THE INVENTION

1. Field of the Invention

The invention concerns filling an analysis card with a liquid medium.

2. State of the Art

"Analysis card" is to be understood as any means, which may or may not be disposable, with which it is possible to perform one or more analyses simultaneously using a single sample and one or more reagents, and to do this in a way that is sealed off from the external environment, the result of the analysis or analyses being obtained optically, for example. Such an analysis card generally comprises a body in which there is formed at least one reading cavity which, during use, receives all or part of the sample and has at least one reagent already present in said cavity, and an orifice communicating with said cavity via at least one internal channel. Said cavity or cavities thus communicate(s) with the outside only via the aforementioned orifice, whilst the card is generally joined to or cooperates with a flexible, external conduit communicating in a leaktight manner with this orifice. It is through this external conduit that it is possible to admit, in the manner described hereinafter, a sample of the liquid medium which is to be analyzed.

Such cards are well known in the prior art and in particular in U.S. Pat. Nos. 3,963,355 and 4,038,151, to which reference will be made as and when necessary.

"Liquid medium" is to be understood as any substance or body which is liquid, at any rate capable of flowing by means of pumping, irrespective of the viscosity or fluidity of this liquid; in particular, where a biological analysis is concerned, the term liquid medium is to be understood as a medium which includes, for example, one or more microorganisms or a biological substance to be analyzed.

As regards the filling of an analysis card as defined above, the procedure to date has been as follows:

—use is made of a sealed chamber, with means for controlling the internal pressure, and in particular the vacuum when said chamber has been depressurized;

—on the one hand, a receptacle, for example a test tube, holding the liquid medium to be sampled or removed, is placed in the chamber, and, on the other hand, alongside the receptacle, the analysis card with the free end of the external conduit immersed in the liquid medium contained by the receptacle;

—the air is evacuated from the chamber until a significant vacuum has been created, for example below 100 mbar absolute, by which means the air is evacuated from the analysis card and the evacuated air passes through the liquid medium in the receptacle;

—after ending the vacuum, and returning the chamber to atmospheric pressure, the liquid medium is aspirated into the analysis card as far as the reading cavity or cavities, which are thus filled.

Such a procedure appears to be particularly contaminating, since the bubbling which occurs as the vacuum is established is capable of projecting particles or droplets of the liquid medium out of the receptacle and thus subsequently into contact with the user or operator, and this despite all the precautions that can be taken in this regard. In the case of a liquid medium containing a pathogenic agent, this seems to be unsatisfactory.

SUMMARY OF THE INVENTION

The subject of the present invention is a method for filling an analysis card in a non-contaminating manner since it proceeds at all times under negative pressure, that is to say without any possibility of the liquid medium used being evacuated to the outside.

According to the present invention, the following steps are carried out in succession:

—to evacuate the gas contained in the analysis card, the free end of the open external conduit is connected in a leaktight manner directly to an evacuation means outside the liquid medium used;

—the external conduit is closed in order to maintain the negative pressure in the analysis card;

—the free end of the closed external conduit is immersed in the liquid medium;

—and the external conduit is re-opened, after immersion of this free end, in order to aspirate the liquid medium into the analysis card.

The present invention also affords the crucial advantage that pumping the gas contained in the analysis card requires limited work and is consequently compatible with relatively simple, even rudimentary, pumping means, in particular manual ones. Moreover, the filling procedure described above can be used both manually as well as in the context of an automatic analysis.

BRIEF DESCRIPTION OF THE DRAWINGS

The present invention is now described with reference to the attached drawing, in which:

FIG. 1 shows a perspective and diagrammatic representation of an analysis card as envisaged by the present invention;

FIG. 3 is a perspective representation of an embodiment of the device shown diagrammatically in FIG. 2;

BRIEF DESCRIPTION OF PREFERRED EMBODIMENTS

Figure 2:
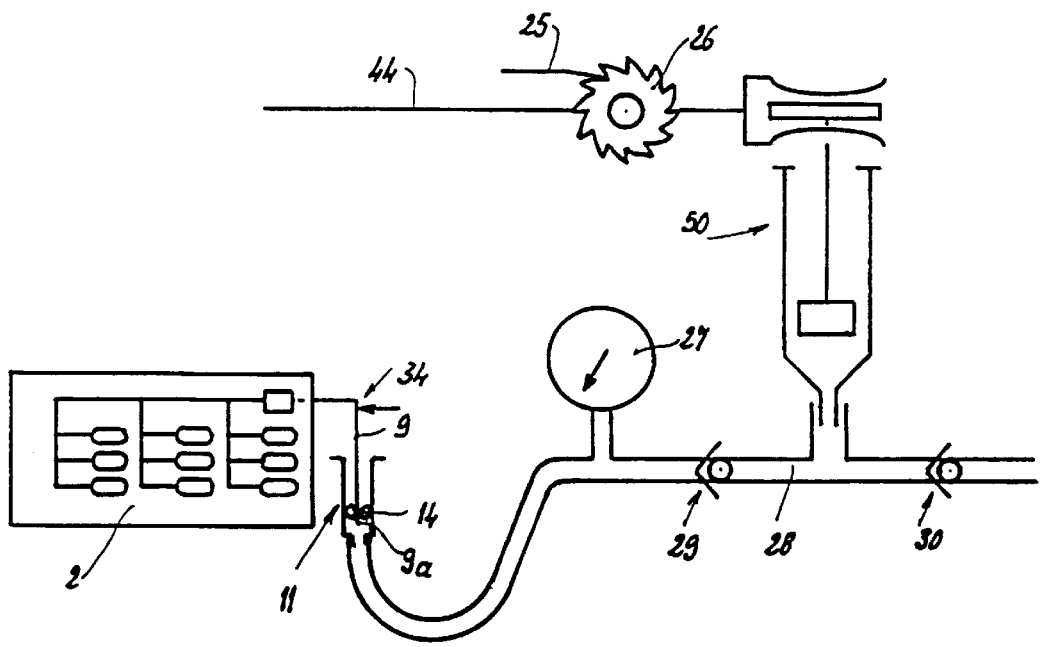
FIG. 2 shows a diagrammatic representation of a filling device according to the invention.

An analysis card 2, treated by the filling method according to the invention, with the device represented in FIGS. 2 and 3, comprises:

—a body 3 made of plastic, molded in a generally flat and rectangular shape, in which there are formed, on the one hand, several series of reading cavities 3a, and, on the other hand, internal open channels 7 as well as an orifice 4;

—two sheets 10 of transparent plastic material which are adhesively bonded in a leaktight manner upon the respective two faces of the body 3;

—and a flexible external conduit 9 having the shape of a bent straw, joined in a leaktight manner to the body 3, at the time of use of the analysis card, including a free end 9a, and an opposite end communicating in a leaktight manner with the orifice 4 after mounting or assembly.

As regards the circulation of the liquid in the card 2, a distributor conduit 5 communicates on one side with the orifice 4 and on the other side with a series of branches 6, to each of which the different reading cavities 3a are connected via respective internal channels 7.

Figure 4:
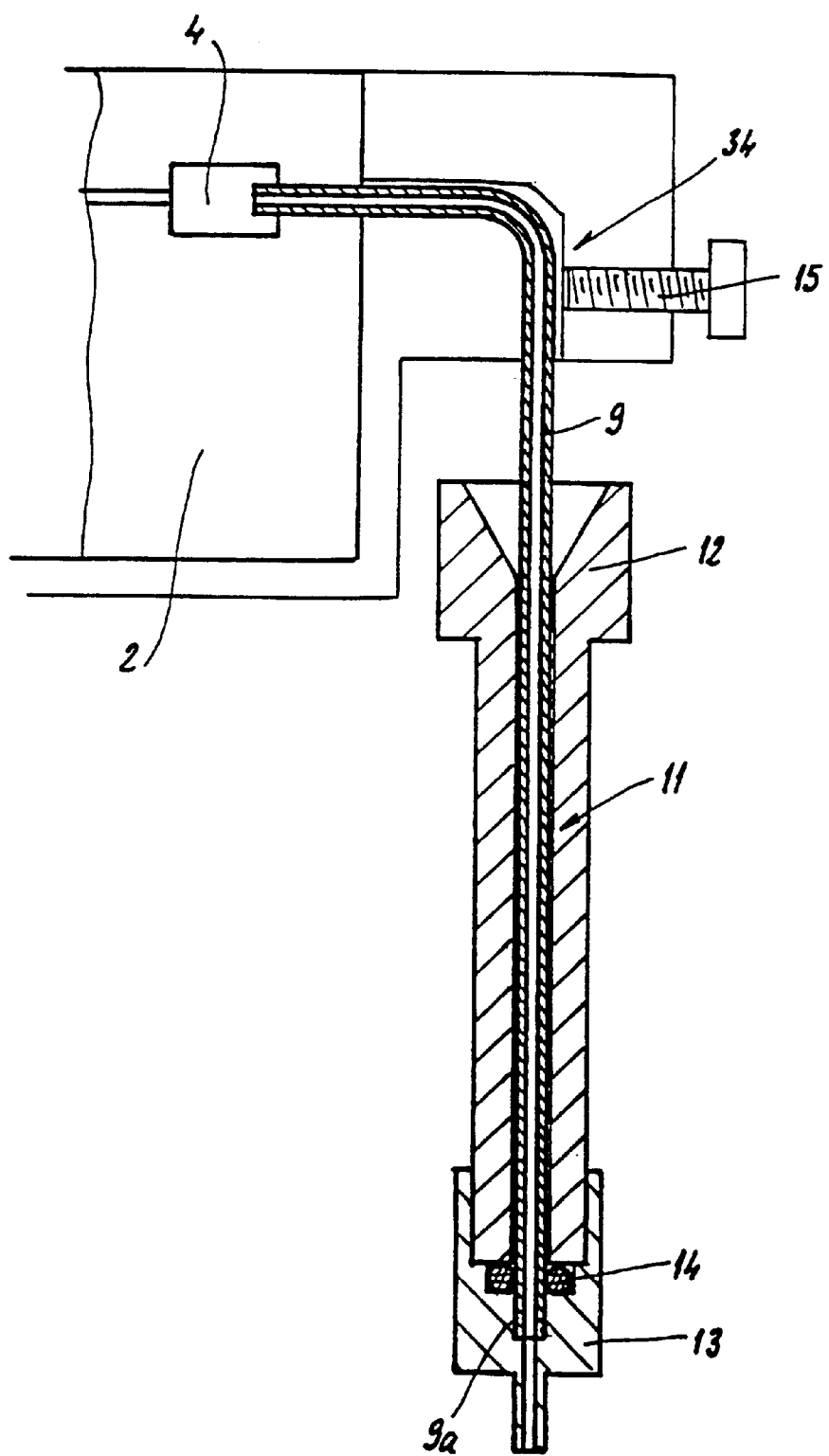
FIG. 4 represents a cross section through the connecting means and the closing means which form part of the device represented in FIG. 3.

In accordance with FIG. 3, a filling device according to the invention comprises:

—a support 18 including a base 19 and a vertical wall comprising two flanks 20a and 20b at right angles;

—a carriage 21 designed to receive and hold the analysis card 2 in a vertical position, with the external conduit 9 in a likewise vertical position; this carriage is capable of sliding against the flank 20a in a controlled manner by virtue of a displacement means 17, and in particular a slide 23;

—another carriage 24 mounted slidably at the bottom of the flank 20b; this carriage is designed to support the tube or receptacle 16 in which the liquid medium 1 to be analyzed is arranged, as well as the connecting means 11 described below;

—an evacuation means 50 consisting of a reciprocating manual pump fitted on the flank 20b and actuated by a lever 44 which can be blocked in rotation by a catch mechanism 26 controlled by an arm 25;

—a connecting means 11, represented more particularly in FIG. 4, comprising on one side a joining piece 12 for sealed and removable coupling to the free end 9a of the external conduit 9, by virtue of an O-ring seal 14, clamped between said joining piece and an abutment piece 13, the latter communicating directly on the other side with the evacuation means 50;

—a means 34 for closing and re-opening the external conduit 9, integral with the carriage 21; this means consist of a screw 15 with which it is possible to pinch the conduit 9; it can be replaced by a valve;

—a pressure gauge 27 for measuring the negative pressure;

—a circuit 28 equipped with flap valves 29 and 30 (FIG. 2) at the outlet of the evacuation means 50, permitting communication between the outlet of the pump and the inlet of the connecting means 11.

With the device filled beforehand, the following filling method can be carried out:

—the analysis card 2 to be filled is placed in the carriage 21 and the closure means 34 is left open;

—the carriages 21 and 24 are moved by way of the displacement means 17 in such a way that the free end 9a of the external conduit 9 communicates in a leaktight manner with the connecting means 11 (see representation in FIG. 4);

—by actuating the lever 44, the gas contained in the analysis card 2 is evacuated, in this case the atmospheric air, and the evacuation pressure is controlled by means of the pressure gauge 27; this may call for one or more backward and forward turns of the lever 44, depending on the capacity of the evacuation means 50; once the desired vacuum has been reached, the lever is fixed in position by means of the catch mechanism 26;

—at this point the external conduit 9 is closed in a leaktight manner using the screw 15;

—by means of a further movement of the carriages 21 and 24, the free end 9a of the external conduit 9 is brought into the receptacle 16, with immersion of this end 9a in the liquid medium 1 contained in the receptacle 16;

—after immersion of this free end, the external conduit 9 is re-opened while keeping the end 9a immersed, which causes aspiration of the liquid medium 1 into the analysis card until each of the reading cavities 3a is filled;

—and the end of the external conduit 9, opposite the free end 9a, is sealed off, the rest of the conduit being separated off and discarded.

At this point the analysis card is filled and is ready for the required analysis procedure, with the results being read off through the different reading cavities 3a.

What is claimed is:

1. A method for filling, with a liquid medium, an analysis card comprising a body in which at least one reading cavity is formed, an orifice communicating with said cavity via at least one internal channel, an external conduit having one end in communication with said orifice and a free end, and a means for closing and opening the external conduit, wherein gas contained in the card is evacuated via said external conduit and the liquid medium is introduced into the evacuated card by immersion of the free end of said external conduit in the liquid medium, said method comprising, in succession:

to evacuate the gas contained in the analysis card, connecting the free end of the open external conduit in a leaktight manner directly to an evacuation means, outside the liquid medium;

closing the external conduit in order to maintain negative pressure in the analysis card;

immersing the free end of the closed external conduit in the liquid medium; and opening the external conduit, after immersion of said free end, in order to aspirate the liquid medium into the analysis card.

2. The method of claim 1, wherein the means for closing and opening the external conduit is a pinching means.

3. The method of claim 1, wherein the means for closing and opening the external conduit is a screw.

4. The method of claim 1, wherein the means for closing and opening the external conduit is a valve.

5. The method of claim 1, wherein the liquid medium is contained in a receptacle, said method comprising, in succession:

connecting said free end of said open external conduit to the evacuation means outside the receptacle, immersing said free end of said closed external conduit in the liquid medium in said receptacle, and opening the external conduit, while maintaining said free end immersed in said receptacle.

6. The method of claim 1, wherein the external conduit is a flexible conduit, wherein closing the conduit is obtained by pinching said conduit, and opening the conduit is obtained by releasing said pinching.

7. The method of claim 1, wherein the evacuation means is a pump.

8. The method of claim 1, wherein the evacuation means is a manual pump.

9. The method of claim 1, wherein the evacuation means is a reciprocating pump.

10. The method of claim 1, wherein the evacuation means is a reciprocating manual pump.

* * * * *